(12) United States Patent
Fukushima et al.

(10) Patent No.: US 12,246,168 B2
(45) Date of Patent: Mar. 11, 2025

(54) NEEDLELESS INJECTORS AND RELATED METHODS

(71) Applicant: AIJEX PHARMA INTERNATIONAL INC., Toyama (JP)

(72) Inventors: Masayoshi Fukushima, Orange, CA (US); Daisuke Futakawa, Takaoka (JP)

(73) Assignee: AIJEX PHARMA INTERNATIONAL INC., Toyama (JP)

( * ) Notice: Subject to any disclaimer, the term of this patent is extended or adjusted under 35 U.S.C. 154(b) by 809 days.

(21) Appl. No.: 17/362,665

(22) Filed: Jun. 29, 2021

(65) Prior Publication Data

US 2022/0409816 A1  Dec. 29, 2022

(51) Int. Cl.
| | | |
|---|---|---|
| *A61M 5/30* | (2006.01) |
| *A61M 5/24* | (2006.01) |
| *A61M 5/28* | (2006.01) |
| *A61M 5/31* | (2006.01) |
| *A61M 5/315* | (2006.01) |

(52) U.S. Cl.
CPC .............. *A61M 5/30* (2013.01); *A61M 5/24* (2013.01); *A61M 5/281* (2013.01); *A61M 5/3129* (2013.01); *A61M 5/315* (2013.01); *A61M 2005/2488* (2013.01)

(58) Field of Classification Search
CPC .......... A61M 5/30; A61M 5/24; A61M 5/281; A61M 5/53129; A61M 5/315; A61M 2005/2488
See application file for complete search history.

(56) References Cited

U.S. PATENT DOCUMENTS 5,704,911 A  *  1/1998 Parsons ............... A61M 5/2033
                                                  604/72
7,806,867 B2 * 10/2010 Willis .................... A61M 5/30
                                                  604/141
2021/0196895 A1 * 7/2021 Lehmann ............. A61M 5/315

* cited by examiner

*Primary Examiner* — Lauren P Farrar
(74) *Attorney, Agent, or Firm* — Alumen IP Law PC

(57) ABSTRACT

A needleless injector for performing a subcutaneous injection without a needle. The needleless injector has a drive end having a drive spring for driving a piston system against a plunger to push liquid out a nozzle of an ampoule with sufficient velocity to deliver a subcutaneous injection without a needle.

19 Claims, 6 Drawing Sheets

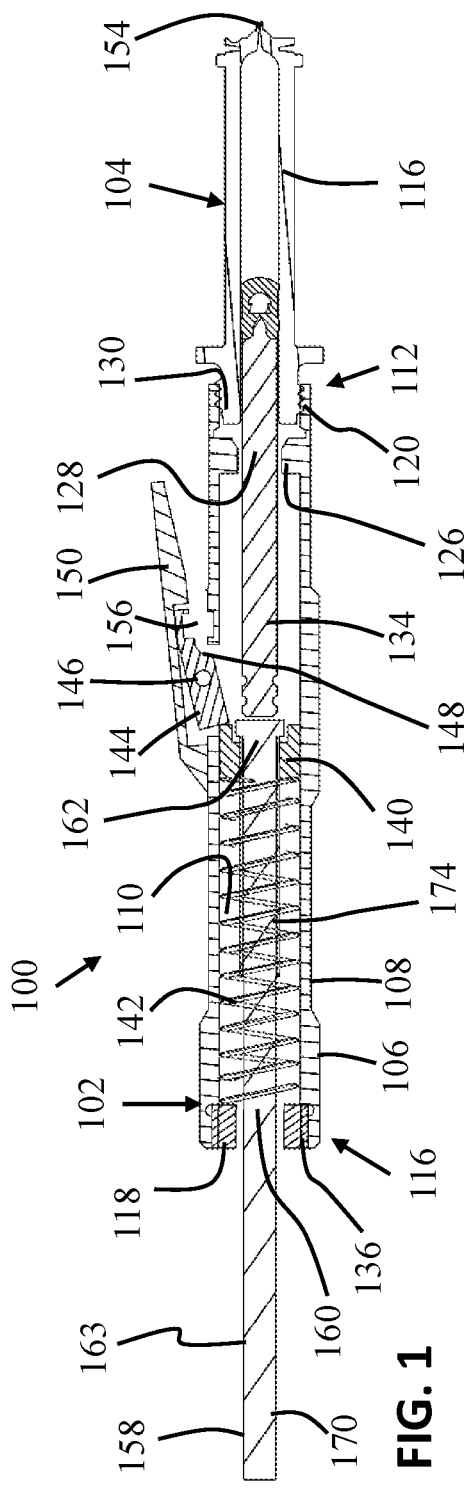
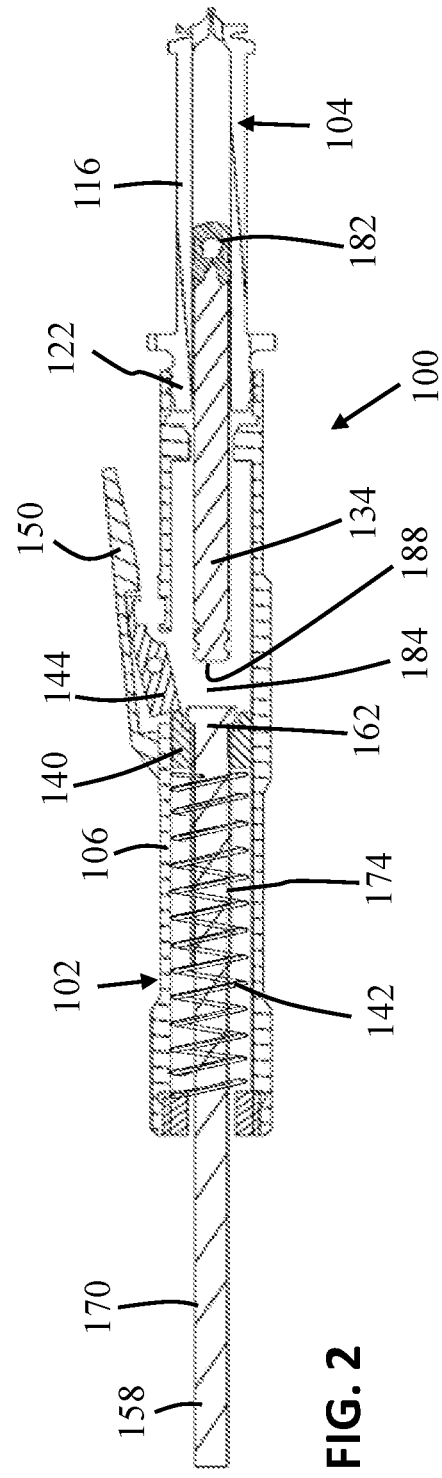
FIG. 1
FIG. 2

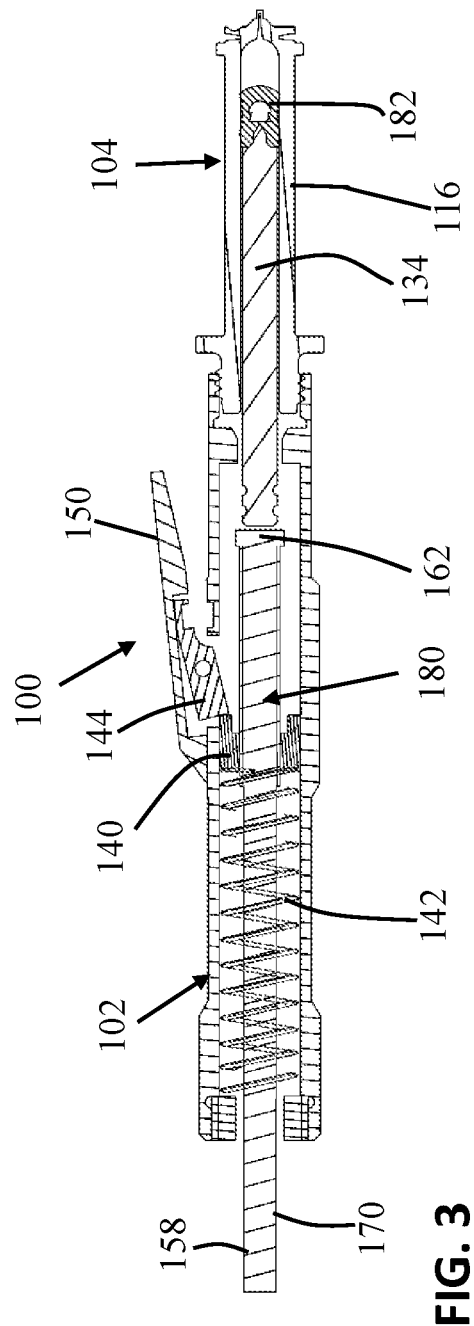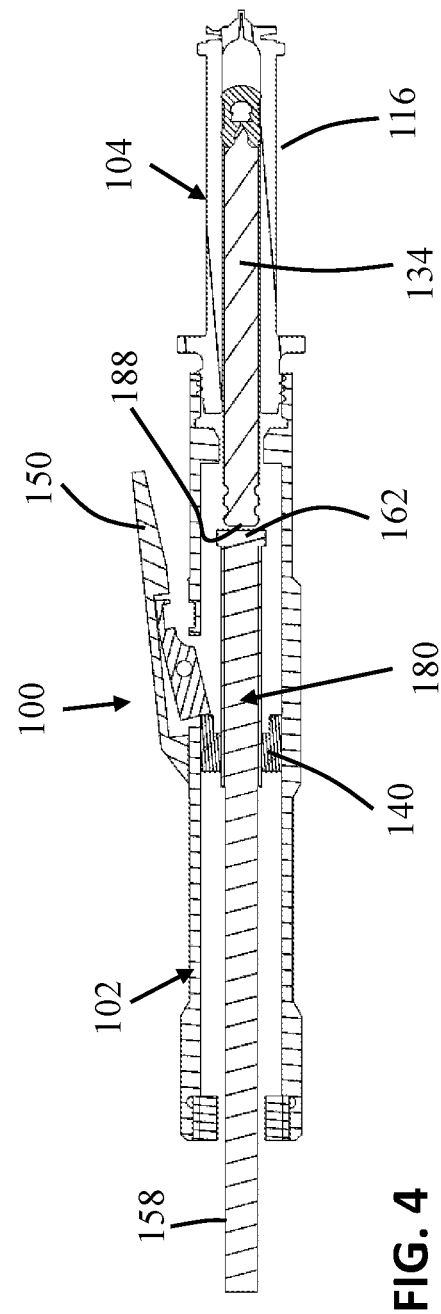

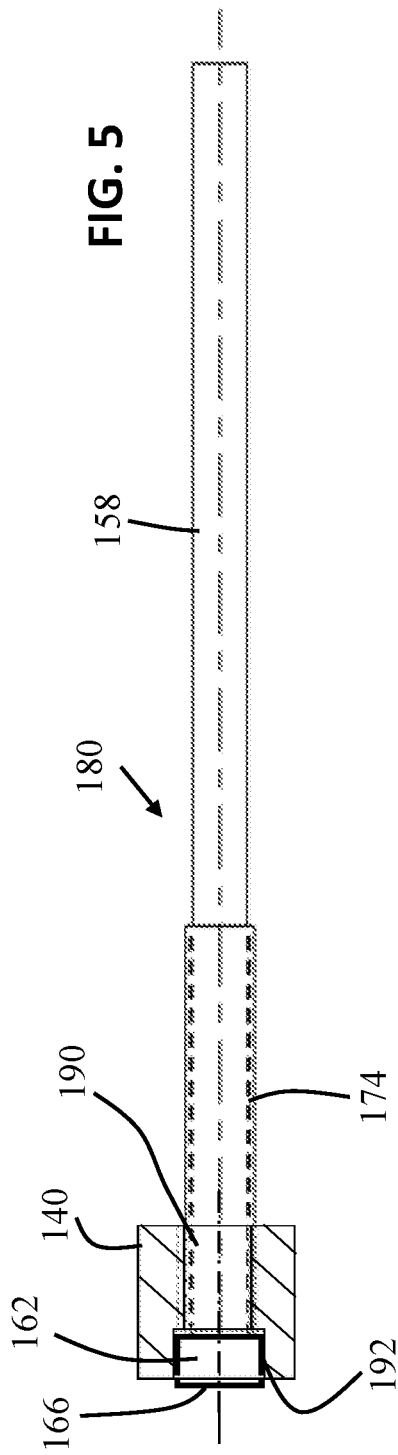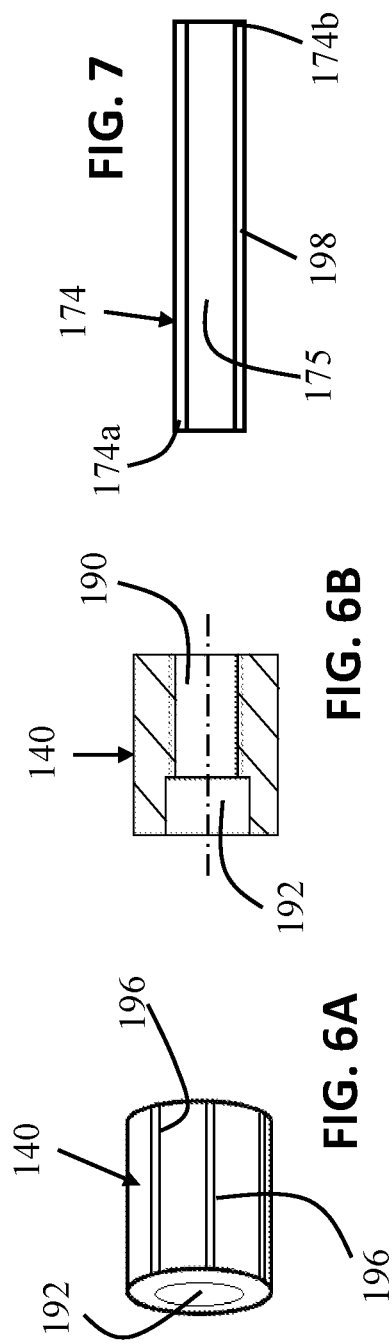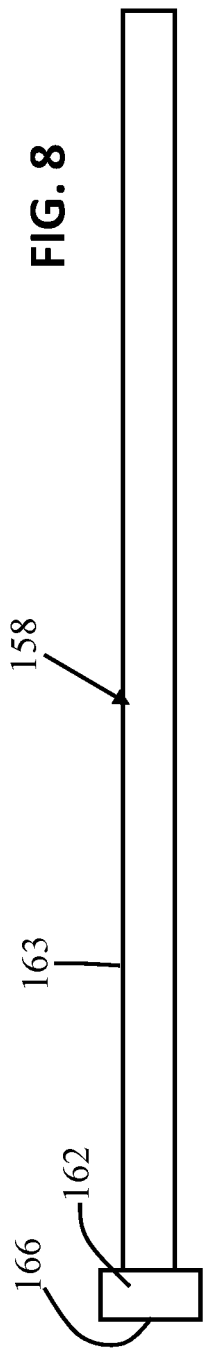

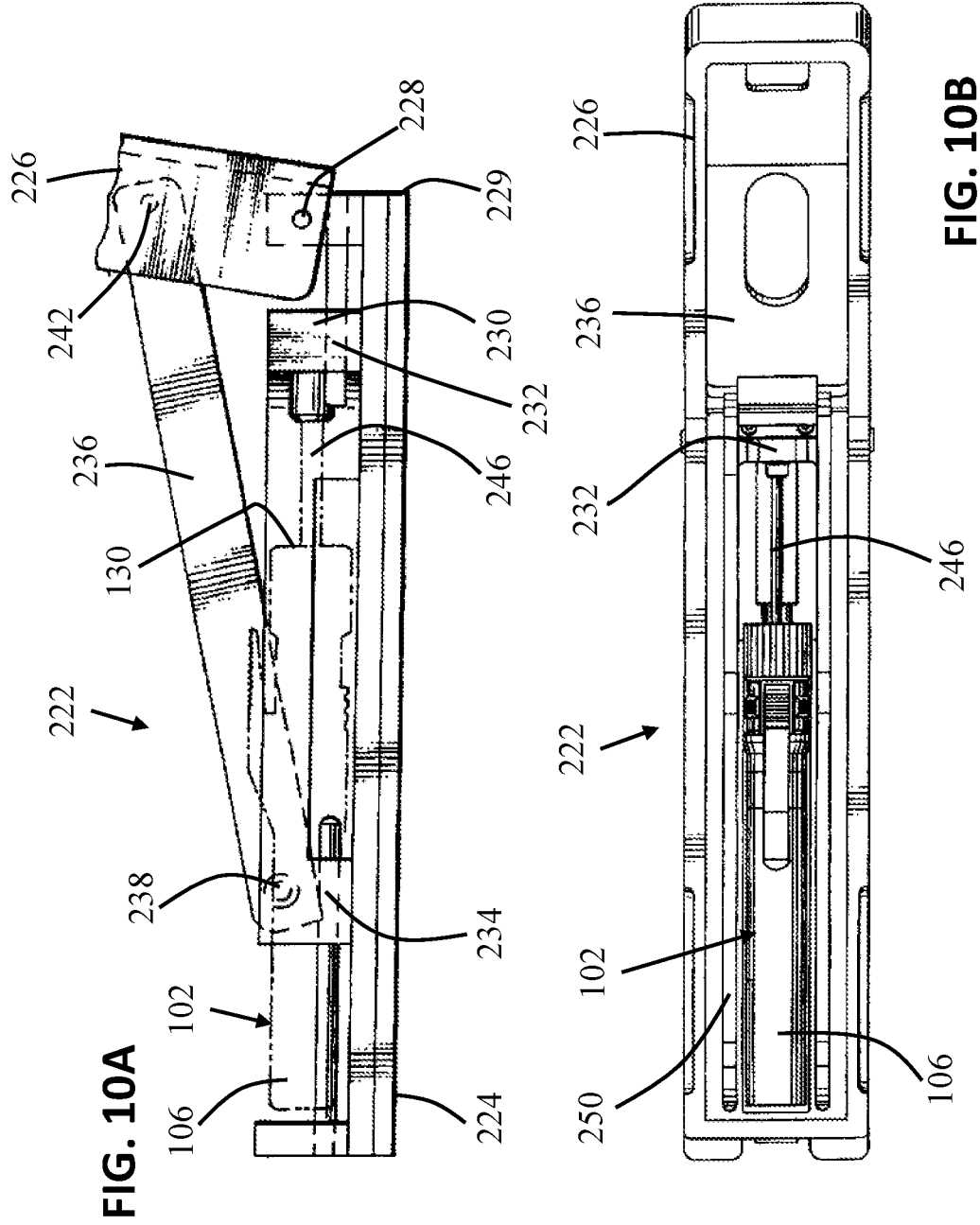

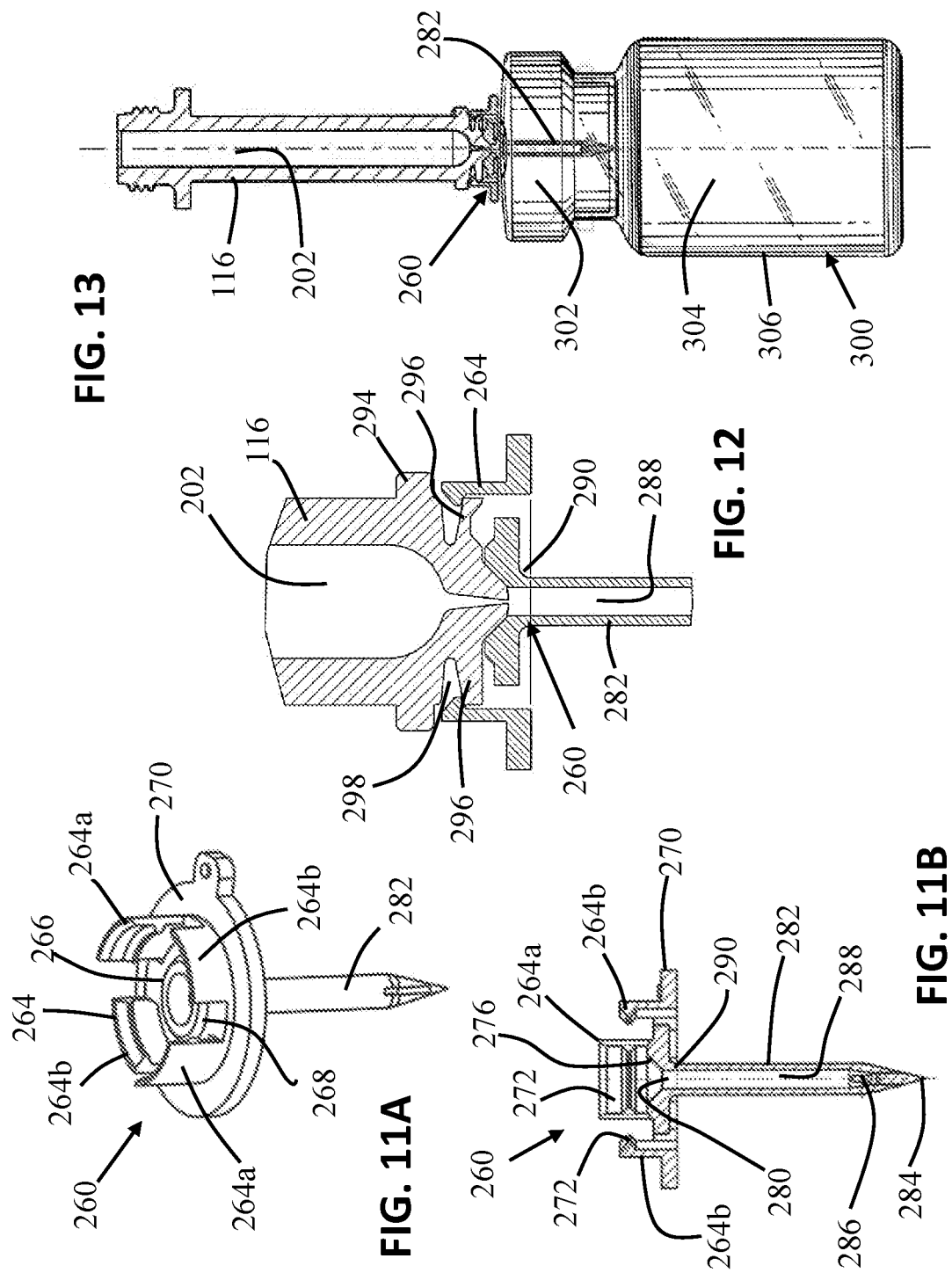

NEEDLELESS INJECTORS AND RELATED METHODS

FIELD OF ART

Needleless injectors are generally discussed with particular discussions on spring actuated needleless injectors that use high pressure liquid streams to pass a medicament or other medicinal fluids through the skin without a needle and wherein the piston system can be adjusted prior to actuation.

BACKGROUND

Needleless injection devices, also known as jet injectors, administer intramuscular and subcutaneous medications without the use of needles. Among the many advantages of jet injection are the reduction of pain and apprehension associated with needles, the elimination of needle stick injuries and the reduction of environmental contamination associated with needle disposal. Jet injection devices are useful in a wide range of drug therapies including immunization vaccines, hormones and local anesthetics, as well as the administration of insulin to the diabetic population, where individuals may require a number of daily injections. Thus, their use has become of increasing interest, particularly by persons of limited physical ability such as the elderly, or the very young.

Injectable medications fall into two different categories; namely, unit dose drugs such as vaccines and analgesics and variable dose drugs such as insulin where the dose size must be adjusted to meet the immediate needs of the individual at the time of administration. When a variable dose is required, as in the case of the administration of insulin, a very accurate amount of medication must be transferred to a variable dose ampoule. Insulin doses are typically marketed in 0.30 ml and 0.50 ml syringe cartridges, as well as provided in bulk in a standard 0.10 ml medication vial. These dose categories and differing medication source containers, therefore, impose conflicting design requirements on ampoules or syringe compartments provided in prior art jet injection systems.

SUMMARY

Aspects of the present invention comprises a needleless injector comprising a drive end and a discharge end. The needleless injector can be used to perform a subcutaneous injection or an intradermal injection. A drive spring can be used to provide the driving force to propel a plunger to perform the injection without a needle. Different drive springs with different spring constants can be used to generate different sprig forces.

An aspect of the invention includes a needleless injector comprising: a force generator comprising a housing with a body having a distal end with an opening, a proximal end enclosed by an end wall having a passage, a side opening, and an interior; a drive spring compressed between the end wall and a piston head having a bore, said piston head being held by a latch piece having a length and a width and pivotably mounted to the housing and holding the piston head against a bias of the drive spring in a ready to use position; a piston rod located in the bore of the piston head, said piston rod having a shaft and a head section, wherein the shaft extends out the passage of the end wall and the head section having a push surface; and wherein the shaft that extends out the passage is rotatable to move the piston rod relative to the piston head and move the push surface away from the piston head in the ready to use position.

The latch piece can project through the side opening of the housing to hold the piston head in the ready to use position.

A trigger can be pivotably mounted to the housing and in contact with the latch piece for rotating the latch piece.

The end wall can be on an end plug and the end plug can be threadedly engaged to the housing.

A collar having a passage can be located in the interior of the housing for stopping distal advancement of the piston head.

The piston head can have an exterior and a recessed cavity and wherein the head section of the piston rod is located in the recessed cavity in the ready to use position.

The recessed cavity can have a diameter and a depth and wherein the depth can be greater than a thickness of the head section.

A plurality of spaced apart channels can be located on the exterior of the piston head.

The piston rod can be made from a thermoplastic or a composite material and the piston head can be made from a metal material.

A coupling sleeve having a bore can have the shaft of the piston rod located in the bore of the coupling sleeve. The coupling sleeve can be located between the piston head and the piston rod.

The coupling sleeve can have exterior threads threadedly engaged with threads in the bore of the piston head.

The shaft of the piston rod and the coupling sleeve can be fixed from relative movement of one another.

The piston head can have a length and wherein the coupling sleeve can have a length that is longer than the length of the piston head.

The coupling sleeve can be made from a metal material and the piston head can be made from a metal material.

A discharge end comprising an ampoule having a barrel with a discharge tip having an orifice and a plunger slidably disposed within the barrel. The barrel can couple to the housing of the discharge end.

The barrel can be threadedly engaged to the housing of the discharge end.

The discharge tip can have an orifice.

A plunger tip can attach to a distal end of the plunger.

The plunger can have an end section with an end surface and wherein the end surface of the plunger can be spaced from the push surface in the ready to use position.

The plunger has an end section with an end surface and wherein the end surface of the plunger can be in contact with the push surface in the ready to use position.

Aspects of the present invention further include a method for manufacturing a needleless injector. The method can comprise: forming a force generator comprising a housing with a body having a distal end with an opening, a proximal end enclosed by an end wall having a passage, a side opening, and an interior; placing a drive spring in the interior of the body between the end wall and a piston head having a bore; holding the drive spring in a compressed state in a ready to use position by holding the piston head with a latch piece having a length and a width and pivotably mounted to the housing to hold the piston head against a bias of the drive spring; placing a piston rod having a shaft and a head section in the bore of the piston head so that the shaft extends out the passage of the end wall; and wherein the shaft that extends out the passage is rotatable to move the piston rod relative to the piston head and move the push surface away from the piston head in the ready to use position.

Aspects of the invention further include a method of filling a discharge end of a needleless injector. The method can comprise: placing a distal end of an ampoule into a receiving space of a vial adaptor, said vial adaptor comprising: a plurality of prongs extending from a flange, each prong comprising a lip and the plurality of prongs comprising a plurality of lips; a gap between two adjacent prongs; a cannula having a lumen, a sharp tip, and an opening at the sharp tip; engaging a gap at the distal end of the ampoule with plurality of lips; and puncturing a septum of a vial with the cannula.

In an example, a needleless injector is structured, sized, and shaped to provide a force to move a fluid through an ampoule with such a velocity that it can be hypodermically injected at an injection site, typically subcutaneously, without a needle. The needleless injector can also be structured, sized, and shaped to provide a force to move a fluid through an ampoule with such a velocity that it can be hypodermically injected at an injection site to perform an intradermal injection without a needle.

A subcutaneous injection is understood to mean an injection that is below the skin. The medicine is typically deposited between the skin and the muscle. Medicines administered subcutaneously can include insulin, some hormones, epinephrine, pain medications, and vaccines, to name a few non-limiting examples. Intradermal injection, often abbreviated ID, is a shallow or superficial injection of a substance into the dermis, which is located between the epidermis and the hypodermis. This route is relatively rare compared to injections into the subcutaneous tissue or muscle. Common injection sites for subcutaneous delivery include the abdomen, arm, and thigh, although other locations of the body are also feasible.

The needleless injector has a force-generating end or drive end and a delivery end or discharge end. The drive end may alternatively be referred to as a force generator and the discharge end may alternatively be referred to as a fluid delivery housing. The force-generating end has a housing with a body having a wall defining an interior cavity. The body can be generally cylindrical and has a first end or coupling end for coupling with the ampoule of the discharge end and a second end or butt-end that has been closed off by an end plug, which can threadedly engage the second end of the housing.

In alternative examples, the end plug can be permanently secured to the housing, such as by welding or by irreversible detents. The end plug can optionally be a plate or alternatively a plate may be used. Both the end plug and the plate have an end wall that covers the proximal end of the housing and wherein the end wall has a passage or a through hole for accommodating sliding movement of the shaft of the piston rod.

The first end or receiving end of the housing has a female threaded receiving socket for threaded engagement with a threaded end of the ampoule. A collar having a passage or opening can be located in the interior cavity proximally of the threaded receiving end. The collar can be situated proximally of the opening a sufficient amount to avoid interfering with the threaded engagement of the threaded end of the ampoule.

In some examples, the collar can act as a bottom for the threaded end to thread against. The opening or passage through the collar can have a diameter that is sized to accommodate axial sliding motion of the plunger, as further discussed below. In an example, the collar, including the passage, may be formed by machining from the opening at the second end and/or the opening at the first end. In other examples, the collar and the passage through the collar may be separately formed and subsequently attached to the housing, such as by snap fit, welding, detents, interference fit, threaded engagement, or combinations thereof.

The housing of the drive end may be made from a metal material, such as from stainless steel, and the collar, if not unitarily formed, may be made from a composite, a thermoplastic material, or a metal material, which can be the same metal material or a different metal material as the housing.

A piston head is slidably disposed inside the interior cavity of the housing. More specifically, the piston head can be urged distally by a helical compression spring, which may be referred to as a primary spring or a drive spring. The drive spring is compressed between the piston head and the end plug and can be held in the compressed state by the latch piece physically blocking the pathway of the piston head.

The latch piece can be pivotably held by a pivot pin to the housing. Flanges or raised shoulders can be provided with the housing to engage the pivot pin. The latch piece can project through a side opening of the housing and held in the loaded or cocked position shown by the distal force of the drive spring. In other examples, the latch piece can push another arm or linkage into the pathway of the drive spring, such as to block the piston head, to then load or cock the drive spring. The latch piece can have a generally rectilinear body with an extension and a hole for accommodating the pin. The latch piece can have a length and a width. In an example, a user can depress the extension or extended end of the latch piece to pivot the latch piece and release the spring to propel the piston assembly to then propel the plunger, as further discussed below.

As shown, a trigger can overly the latch piece, which can seat in a cutout or recessed section of the trigger. In other examples, the latch piece can have an extended length and be used without the trigger. When used, the trigger and the latch piece may both be pivotable about the same pin, which can be held at ends thereof by receiving holes formed on two spaced apart side flanges (not shown).

In an example, the housing can be provided with two spaced apart wall structures or flanges each with an opening for receiving a respective end of the pivot pin. The flanges can be machined with the housing, or be attached to the housing, such as by welding or by fasteners. The trigger lengthens the extension of the latch piece to provide additional leverage when depressing the trigger to rotate the latch piece to then release the drive spring. A safety mechanism, such as a movable ring or a safety pin, may be used to obstruct the trigger and wherein the safety mechanism can be moved or removed, such as slid away from the trigger, before the trigger can be activated.

In some examples, a return spring (not shown) can be provided between the trigger and the housing, at the complementary receiving area. The return spring can bias the contact end of the trigger away from the housing so that the trigger pushes the latch piece downward into the side opening to engage the piston head to thereby hold the drive spring in the compressed state.

When the trigger is pressed to release the primary or drive spring, the return spring can push the trigger upward, or the opposite direction, to then push the latch piece downwardly so that the primary spring can be reset for another needleless injection, as further discussed below.

The drive spring can be biased between the end plug and the piston head. It has been found that the coiled spring should develop approximately 25 pounds or greater force in order propel the piston system to then propel the plunger to generate sufficient discharge pressure at the discharge tip of the ampoule, to penetrate a wide range of skin thickness with just fluid jet pressure without a needle.

The spring pressure can vary depending on the injection site. For example, when used to apply numbing medicines for dental procedures or to apply hyaluronic acid to the facial area which has softer and/or thinner skin, or when performing an intradermal injection, the spring pressure can be less than 25 pounds to generate less delivery force at the discharge end. Preferably, the spring in combination with the length of the piston system and the length of the plunger inside the ampoule should have sufficient length to generate the driving spring force at the discharge tip. In other words, the drive spring can be calibrated to operate between two ends of its full stroke.

A piston rod can pass through the passage or bore of the end plug. The passage or bore should have a sufficient inside diameter (ID) so that the shaft of the piston rod can slide with adequate clearance. The piston rod has a head section and a rod or shaft section. The head section has a push surface that contacts the plunger to move the plunger when the spring is released, as further discussed below. The rod or shaft has an overall length measured from the end most proximal end to where the rod connects to the head section. Part of the overall length of the rod extends proximally of the proximal end of the housing, which may be referred to as a control rod section.

The control rod section can vary in length depending on the position of the piston rod relative to the piston head. For example, once the spring is loaded or cocked by compressing the drive spring and then holding the drive spring in the compressed state by the engaging the piston head with the latch piece, a length of the control rod section extends out the end plug. The length of the control rod section that extends proximally out of the end plug can vary as the piston rod can independently move relative to the piston head by adjusting the control rod section.

In an example, the piston rod is threadedly engaged to a coupling sleeve (FIGS. 5 and 7) of the piston system and the coupling sleeve can fix to the piston head such that the sleeve and the piston head do not move relative to one another, such as by interference fit, by using a set screw, by welding, or a combination thereof. Thus, when the control rod section is gripped and rotated, its position relative to the coupling sleeve and to the piston head moves or shifted. For example, when the control rod section is rotated in a clockwise direction, the rod or shaft can advance in the distal direction to then move the head section of the piston rod in the distal direction relative to the piston head. This in turn can push on the plunger to advance the plunger further within the ampoule without releasing the spring.

In practice, by adjusting the plunger rod, a user can adjust the volume within the ampoule or can dispense trapped air within the ampoule before using the needleless injector on a patient. In an example, the proximal end, at the control rod section, can be enlarged to facilitate gripping. Optionally, a flared end or a knurled end or finish can be provided at the proximal end to facilitate gripping the proximal end. Still alternatively, a sleeve can be placed over the proximal end to provide a tactile grip.

In an example, the control rod section can be rotated counter-clockwise relative to the coupling sleeve to move the rod or shaft in the proximal direction and clockwise to move the rod in the distal direction relative to the coupling sleeve. In alternative embodiments, the rotation direction and the rod movement direction can reverse. As used herein, distal end denotes an end closer to where fluid exits the ampoule, and the proximal end is the opposite end.

In an alternative and more preferred embodiment, the piston rod can be fixed to the coupling sleeve such that the piston rod and the coupling sleeve do not move relative to one another. For example, the piston rod and the coupling sleeve can engage by interference fit, by crimping, by set screw, or equivalents, such that the two do not move relative to one another. The coupling sleeve is then threadedly engaged to the threaded bore of the piston head such that rotation of the control rod section changes the threaded engagement between the coupling sleeve and the threaded bore of the piston head. That is, when the control rod section is rotated clockwise, both the piston rod and the coupling sleeve advance within the threaded bore of the piston head to advance the head section of the piston rod in the distal direction. In still yet other examples, the piston rod can threadedly engage the piston head directly without utilizing the coupling sleeve. Again, the rotation direction and the rod movement direction can reverse such that a counter-clockwise direction advances the piston rod in the distal direction.

When mounting the discharge end to the drive end, the plunger extends out the proximal end of the ampoule. Depending on the length of the plunger, how much medication is filled in the interior of the ampoule, or both, the proximal end-most point of the plunger can either push against the piston system and force some medication to discharge out the discharge tip, can mate up to the push surface of the piston system, or can be spaced from the push surface of the piston system.

The needleless injector can be configured, such as sized and shaped, so that when the ampoule is filled to a maximum filled line, the length of the plunger that extends out the ampoule just mate up to the push surface of the piston system without the piston system pushing against the plunger to discharge some liquid out the discharge tip of the ampoule. Nonetheless, a user may still want to adjust the piston rod by rotating the control rod section to move the head section and the push surface closer to or into contact with the end surface of the plunger. Further movement of the head section, by moving the piston rod relative to the piston head, can move the plunger to force out air that may be trapped in the ampoule.

Optionally, the user may want to purposely dispense some medications to get down to a desired dosage before performing the needleless injection. To do so, the user can grab the control rod section and rotate to advance the head section of the piston rod into the plunger to move the plunger further into the ampoule, to dispense some medications out the distal tip.

In an example, when the piston rod is adjusted to either dispense trapped air in the ampoule and/or to dispense medications to get down to a desired dosage inside the ampoule, the piston head and/or the head section is in contact with the plunger prior to depressing the trigger to release the drive spring. Thus, upon actuating the trigger to release the spring, no impulse impact is made by the propelling the piston system against the plunger, by not having a gap between the two, which can reduce sound emitted by the needleless injection process. In other examples, a gap can be provided between the piston system and the plunger, which can discharge liquid out the discharge end of the ampoule with sufficient force to perform a subcutaneous needleless injection, but possibly with a louder sound.

An ampoule that is connected to the drive end can be filled with a lower or smaller volume and therefore the plunger and the plunger tip attached to the plunger can be located further distally inside the ampoule. Thus, there can be a gap between the proximal end-most part of the plunger and the head section of the plunger system compared to the needleless injector. The trigger can be activated to discharge the spring, with the gap prior to releasing the drive spring. However, the piston rod can be adjusted to take up the gap before the trigger is activated, as further discussed below.

In an example, the ampoule is filled with a lower or smaller volume and therefore the plunger and the plunger tip attached to the plunger are located further distally inside the ampoule. Thus, there can normally be a gap between the proximal end-most part of the plunger and the head section of the plunger system. However, the piston rod can be adjusted by rotating the control rod section to advance the piston rod, and the coupling sleeve that the piston rod is attached to, relative to the piston head to take up the gap before the trigger is activated. Consequently, the control rod section of the rod or shaft 163 that extends out the end plug can be relatively short.

In an example, the head section of the piston rod is advanced distally of the piston head. As the piston rod is secured to the coupling sleeve, the distal end of the coupling sleeve moves further distally of the piston head and the proximal end of the coupling sleeve moves closer to the piston head. To prevent over rotation and possibly causing the coupling sleeve to completely separate from the piston head, the coupling sleeve and/or the piston head may incorporate limiting features to stop the relative rotation between the two, such as pins, rods, flat portions without threads, projections, etc. Again, alternative embodiments of the present invention include directly threading the piston rod to the piston head without the coupling sleeve.

When a user depresses the trigger, movement of the trigger can cause the latch piece to rotate about the pivot pin to then separate from the piston head. No longer held by the latch piece, the spring force of the drive spring expands to propel the piston system, which includes the piston rod, coupling sleeve, and piston head, in the distal direction. This movement can cause the head section to push against the end surface of the plunger to advance the plunger in the distal direction with sufficient force such that the plunger tip 182, which slidingly seals against the interior of the ampoule, to then force medications contained in the ampoule to expel out the discharge tip to then penetrate under the skin to deposit discharged medications under the skin.

Distal travel of the head section can stop when the trigger is activated by sizing the head section to contact or abut the collar in the interior of the housing. Doing so can prevent the piston system from driving the plunger tip violently or excessively into the discharge end of the ampoule.

The piston head can have a threaded bore for threaded engagement with the exterior threads of the coupling sleeve. A recessed cavity is provided at the distal end of the piston head for receiving the head section of the piston rod. The recessed cavity is sufficiently shallow and wide to receive the head section so that the push surface of the head section is exposed for abutting contact with the end section of the plunger.

In some examples, the recessed cavity is eliminated and the piston head comprises the threaded bore only. In this alternative embodiment, the proximal side of the head section can abut or contact the distal end surface of the piston head when the piston system is in the corresponding position.

In an example, the length of the coupling sleeve is about two times to about five times the length of the threaded bore of the piston head. In other examples, the length of the coupling sleeve can be greater than five times longer, such as six to eight times longer. The length of the coupling sleeve relative to the length of the threaded bore controls the length of adjustment that the control rod section can be rotated to move distally to push the plunger in the distal direction, after the drive spring is loaded or cocked.

A large range of adjustment allows the plunger to move within the ampoule to adjust the fluid contents within the ampoule from a full ampoule to about 20% of the total volume. For example, the contents of the ampoule can be adjusted from about 0.50 mL down to about 0.10 mL. In other examples, the contents can be adjusted down to a lower volume, such as down to about 0.05 mL. The size of the ampule can be modified accordingly to accommodate dosages other than as described, which may require also adjusting the spring constant and plunger size.

In an example, a plurality of spaced apart channels are formed on the exterior of the piston head. The channels can each extend lengthwise, the same direction as the bore. The channels can provide venting to minimize possible vapor or air lock when the piston head is propelled by the drive spring. In other examples, the channels can be omitted and the outside diameter of the piston head can be sized with the interior diameter of the housing, to allow sufficient clearance therebetween, to permit venting without the channels. In still other examples, the interior of the housing can be provided with vent channels. The piston head can be machined from a metal material, such as stainless steel.

The coupling sleeve can have exterior threads for engaging the threaded bore of the piston head. The threads in the bore of the piston head and on the exterior of the sleeve are complementary and can range from course threads to fine threads to enable either coarse adjustments or fine adjustments. The coupling sleeve has a bore for receiving the rod or shaft of the piston rod, in an interference or in a fixed arrangement, such as with a set screw, adhesive, tongue and groove, and equivalents thereof.

The piston rod can have an elongated rod or shaft, a head section at a distal end of the shaft, which can be generally disc-shape with a thickness and a push surface at a distal end thereof. The head section can have a diameter that is about 1.5 to 4 times the diameter of the shaft. The piston rod can be made from a composite or a thermoplastic material. Where the piston rod threads directly to the threaded bore of the piston head without the coupling sleeve, the piston rod can be made from a composite, a thermoplastic material, or a metal material.

The discharge end of the needleless injector can comprise an ampoule and a plunger slidably disposed within the interior of the ampoule. The ampoule can comprise a barrel having an enclosed distal end with a discharge tip having a passage or orifice extending therethrough defining a nozzle. The passage or orifice is in fluid communication with the interior and liquid in the interior, such as medications, can dispense out through the nozzle when pressurized by the propelling plunger.

The nozzle opening or size can be between about two thousandths to about six thousandths of an inch but can vary depending on the generated velocity and pressure for performing a needleless injection. In an example, the inside diameter of the barrel is about 0.18-inches and the length from the flange to the enclosed distal end is about 1.4-inches. The ampoule can accommodate or hold up to about 0.50 mL. However, these values are exemplary only as the size of the ampoule can vary, such as holding up to about 0.30 mL only or greater than 0.50 mL.

The threaded end at the proximal end of the barrel comprises male threads for engaging corresponding female threads of the threaded receiving socket of the drive end. The flange can serve as a physical stop for the engagement but the threaded end can instead bottom out in the receiving socket before the flange is contacted by the rim of the first open end.

The ampoule may be made from a hard but brittle-resistant thermoplastic material. The ampoule may be made from plastic injection molding, such as with polycarbonate (PC), ABS, LEXAN, or Acrylic, as non-limiting examples. The exterior of the barrel can be provided with markers or scales, such as 0.10 mL, 0.20 mL, etc., to aid in measuring the volume of medications added to the interior of the barrel.

The plunger can be partially located inside the interior and partially extending out the proximal opening of the barrel. The plunger can have a shaft with a distal end having a mounting tip that projects into a sleeve like interior of the plunger tip to retain the plunger tip at the distal end of the plunger. The plunger tip can slidingly seal against the interior wall surface of the barrel and compresses the liquid as it advances in the distal direction to build pressure to then eject out of the nozzle with sufficient velocity that it can be hypodermically injected at an injection site without a needle. The plunger tip can be made from an elastomeric material, such as polytetrafluoroethylene (TPFE) or a rubber material, or a thermoplastic-elastomer (TPE) material. The plunger tip can have a generally round outer cylindrical shape with a length and wherein the exterior of the plunger tip can have one or more undulating or grooved surfaces to form a discontinuous contact with the interior surface of the barrel.

The plunger can be about 2.1-inches to about 2.3-inches in overall length and about 0.175-inches in diameter. In other examples, the plunger can have a different length and diameter without deviating from the scope of the invention. The plunger can be made from the same or similar material as the material of the ampoule or can be made form a different material. As shown, the plunger has an end section 188 with a plurality of spaced apart grooves. The grooves can be provided for aesthetic reasons but can optionally be omitted.

A resetter can be provided to reset the primary or drive spring of the drive end. The resitter can comprise a base housing and a cover handle connected to the base housing by a pin, which is located near the far housing end. The cover handle can have a wall surface that covers the upper opening of the base housing. When rotated to close over the upper opening of the base housing, the cover handle can have approximately the same length as the base housing.

A saddle is slidably mounted to the base housing of the resetter. The saddle has a push head having a length and a width and the push head is connected to a first pair of linkage arms. Each linkage arm is shaped similar to a spatula or elongated flat stick. Each of the first pair of linkage arms is in turn connected to a respective pair of second linkage arms by a set of pins. Each of the second pair of linkage arms is in turn connected to the cover handle, via two separate pins or a single pin that connects to both linkage arms of the second pair.

The upper pin can snap into a pin receptacle secured to or unitarily formed with the cover handle. Thus, when the cover handle moves to the raised position, the first and second pair of linkage arms are moved by the cover handle and therefore move the push head to the first or retracted position shown. When the cover handle is lowered to a closed position, the linkage arms move the push head to the second or load position, which moves to the left of the far housing end.

A press rod or shaft can be mounted to the push head. Thus, when the push head moves between the first position or the retracted position and the second position or the load position further left of the far housing end, due to movement of the cover handle and the linkage arms, the movement moves the press rod. This movement of the press rod can be used to reset the drive spring, as further discussed below.

The drive end can be reset using the resetter for re-use after the drive spring is released by the trigger. As shown, the housing of the drive end is positioned in the loading space of the base housing with the open end of the housing oriented towards the push head and the press rod projecting through the open end and into the housing of the drive end. The free end of the press rod, the end opposite the end that attaches to the push head, is placed in contact with or in close proximity to the piston system, and more particularly to the push surface of the piston rod.

The cover handle can be rotated counter-clockwise about the pin from the orientation shown to close the cover handle over the base housing. This motion moves the two pairs of linkage arms and the linkage arms move the push head from the retracted position to the load position, which moves the press rod to push the head section of the piston rod and the piston head towards the end plug of the drive end to compress the drive spring.

As the piston head moves proximal of the latch piece by the press rod of the resetter, the tip of the latch piece, acted on by the return spring, moves in front of the piston head to hold the drive spring in the compressed position. This action causes the drive spring to be reset or cocked so that the drive end can be used for another subcutaneous injection.

After the drive spring is reset, the cover handle can be lifted, raised, or rotated in the clockwise direction to open the resetter to thereby allow the drive end to be removed from the loading space of the base housing. To use the drive end that has now been reset using the resetter, an ampoule filled with medications can be threaded into the open threaded receiving socket of the housing of the drive end, as previously discussed.

A vial adaptor can be sized and shaped to couple an ampoule to enable filling the interior of the ampoule with a medicament or medication from a vial. The vial adaptor comprises a plurality of prongs. In an example, the prongs are spaced apart and together define a holding space or receiving space for receiving the distal end of the ampoule. In an example, each prong is generally rectangular and arcuate or arc shape. The plurality of prongs together defining a generally round collar having gaps between adjacent prongs.

In an example, four prongs can be provided extending above a flange. In an example, the four prongs have two sets of two prongs that are the same. For example, two opposing taller prongs extend higher above the flange than two opposing shorter prongs. Each of the two sets of prongs has a detent or radial lip. Thus, the two taller prongs have radial lips that are elevated higher than the radial lips of the shorter prongs.

The different heights can be incorporated for the two different radial lips to engage different thread sections located at the distal end of the ampoule. Thus, when the distal end of the ampoule is placed into the receiving space of the vial adaptor, the different radial lips can grip the differently arranged thread sections located on the ampoule. If the ampoule has different threads or flange sections at the distal end, the prongs and the radial lips can be adjusted accordingly to mate between the two.

The flange on the vial adaptor can have a raised central rim and a central bore. The raised central rim can be sized and shaped to surround and abut the raised distal tip of the ampoule to form a tight connection with the ampoule. A cannula having a sharp tip and an opening, such as to a side of the sharp tip, can be provided at an end of the cannula. The opening at the tip can be in fluid communication with the lumen passing through the cannula. The cannula can have a length measured from its base to the sharp tip. The length of the cannula can be selected to fit a range of vial sizes.

In an example, the ampoule can comprise a flange and a continuous or spaced apart mounting flange sections located distally of the flange and having a gap therebetween. The mounting flange sections can be configured to be gripped by the prongs on the vial adaptor and the radial lips or detents can project into the gap to grip the ampoule. The ampoule can engage the vial adaptor using the quick snap connection of the prongs. In other examples, the vial adaptor can incorporate a threaded receptacle to threadedly engage the ampoule.

Methods of making and of using needleless injectors, vial adaptors, and resetters and components thereof discussed herein are within the scope of the present invention.

BRIEF DESCRIPTION OF THE DRAWINGS

These and other features and advantages of the present devices, systems, and methods will become appreciated as the same becomes better understood with reference to the specification, claims and appended drawings wherein:

FIG. 1 is a schematic side view of a needleless injector having a discharge end and a drive end.

FIG. 2 is a schematic side view of a needleless injector having a discharge end and a drive end with the plunger of the discharge end spaced from the piston system.

FIG. 3 is a schematic side view of a needleless injector having a discharge end and a drive end with the piston rod positioned distally relative to the piston head and in contact with the plunger.

FIG. 4 is a schematic side view of the needleless injector of FIG. 3, shown without the drive spring.

FIG. 5 is a schematic cross-sectional side view of a piston system having a piston head, a piston rod, and a coupling sleeve.

FIGS. 6A and 6B show a perspective view and a cross-sectional side view, respectively, of a piston head.

FIG. 7 is a schematic cross-sectional side view of a coupling sleeve.

FIG. 8 is a side view of a piston rod.

FIG. 10A is a side view of a resetter for resetting the drive spring of the needleless injector drive end FIG. 10B is a top view of the resetter.

FIG. 11A is a perspective view of a vial adaptor and FIG. 11B is a cross-sectional side view thereof.

FIG. 12 is a partial cross-sectional side view of an ampoule engaging a vial adaptor.

FIG. 13 is a side view showing an ampoule engaging a vial adaptor and the cannula of the vial adaptor penetrating the septum of the vial.

DETAILED DESCRIPTION

Figure 9:
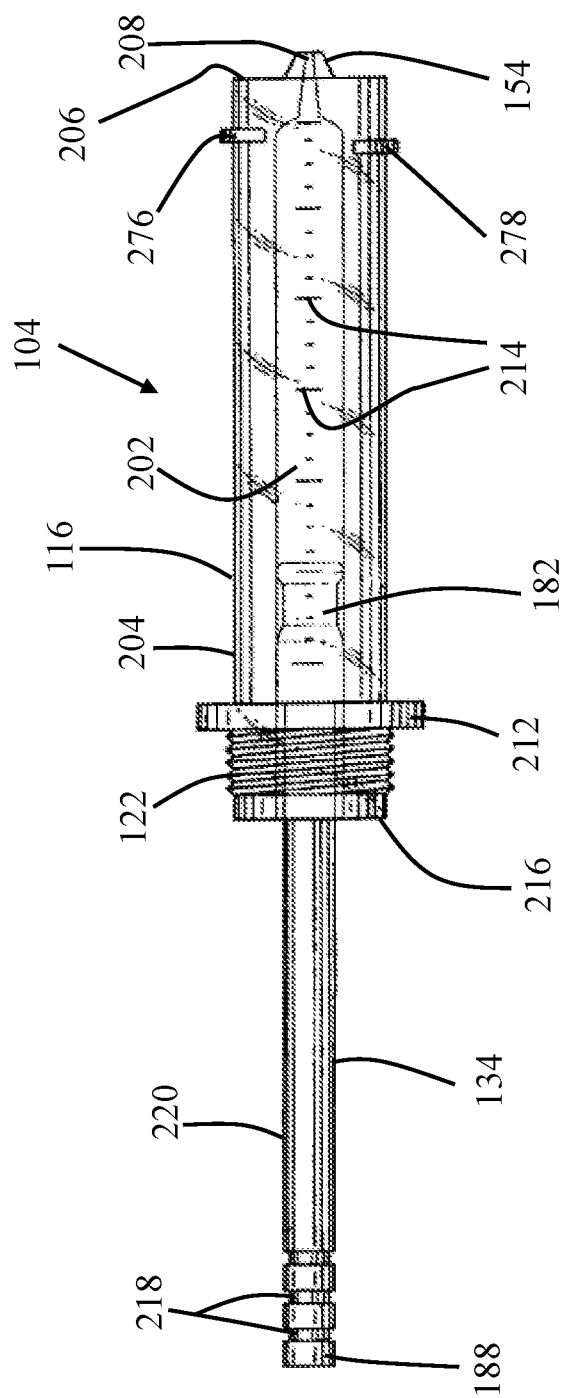
FIG. 9 is a side view of an ampoule and a plunger.

The detailed description set forth below in connection with the appended drawings is intended as a description of the presently preferred embodiments of needleless injectors provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

With reference now to FIG. 1, a schematic cross-section side view of a needleless injector 100 in accordance with aspects of the invention is shown, shown in a ready to use position with the spring compressed and ready for triggering. The needleless injector 100 is structured, sized, and shaped to provide a force to move a fluid through an ampoule with such a velocity that it can be hypodermically injected at an injection site, typically subcutaneously, without a needle. The needleless injector 100 can also be structured, sized, and shaped to provide a force to move a fluid through an ampoule with such a velocity that it can be hypodermically injected at an injection site to perform an intradermal injection without a needle. A subcutaneous injection is understood to mean an injection that is below the skin. The medicine is typically deposited between the skin and the muscle. Medicines administered subcutaneously can include insulin, some hormones, epinephrine, pain medications, and vaccines, to name a few non-limiting examples. Intradermal injection, often abbreviated ID, is a shallow or superficial injection of a substance into the dermis, which is located between the epidermis and the hypodermis. This route is relatively rare compared to injections into the subcutaneous tissue or muscle. Common injection sites for subcutaneous delivery include the abdomen, arm, and thigh, although other locations of the body are also feasible.

The needleless injector 100 has a force-generating end or drive end 102 and a delivery end or discharge end 104. The drive end 102 may alternatively be referred to as a force generator and the discharge end 104 may alternatively be referred to as a fluid delivery housing 104. The force-generating end 102 has a housing 106 with a body 108 having a wall defining an interior cavity 110. The body 108 is generally cylindrical and has a first end or coupling end 112 for coupling with the ampoule 116 of the discharge end 104 and a second end or butt-end 116 that has been closed off by an end plug 118, which can threadedly engage the second end 116 of the housing 106. In alternative examples, the end plug 118 can be permanently secured to the housing, such as by welding. The end plug can optionally be a plate or alternatively a plate may be used. Both the end plug and the plate have an end wall that covers the proximal end of the housing and wherein the end wall has a passage or a through hole for accommodating sliding movement of the shaft of the piston rod 158.

The first end or receiving end 112 of the housing 106 has a female threaded receiving socket 120 for threaded engagement with a threaded end 122 of the ampoule 116. A collar 126 having a passage or opening 128 is located in the interior cavity proximally of the threaded receiving end 120. The collar 126 is situated proximally of the opening 130 a sufficient amount to avoid interfering with the threaded engagement of the threaded end 122 of the ampoule. In some examples, the collar 126 acts as a bottom for the threaded end 122 to thread against. The opening or passage 128 through the collar 126 has a diameter that is sized to accommodate axial sliding motion of the plunger 134, as further discussed below. In an example, the collar 126, including the passage 128, may be formed by machining from the opening 136 at the second end 106 and/or the opening 130 at the first end 112. In other examples, the collar and the passage through the collar may be separately formed and subsequently attached to the housing 106, such as by snap fit, welding, detents, interference fit, threaded engagement, or combinations thereof. The housing 106 may be made from a metal material, such as from stainless steel, and the collar, if not unitarily formed, may be made from a composite, a thermoplastic material, or a metal material, which can be the same metal material or a different metal material as the housing.

A piston head 140 is slidably disposed inside the interior cavity 110 of the housing 106. More specifically, the piston head 140 is urged distally by a helical compression spring 142, which may be referred to as a primary spring or a drive spring. The spring 142 is compressed between the piston head 140 and the end plug 118 and held in the compressed state by the latch piece 144 physically blocking the pathway of the piston head 140. The latch piece 144 is pivotably held by a pivot pin 146 to the housing 106. Flanges or raised shoulders can be provided with the housing 106 to engage the pivot pin 146. The latch piece 144 projects through a side opening 148 of the housing and held in the loaded or cocked position shown by the distal force of the drive spring 142. The latch piece 144 has a generally rectilinear body with an extension and a hole for accommodating the pin 146. The latch piece 144 has a length and a width. In an example, a user can depress the extension or extended end of the latch piece to pivot the latch piece 144 and release the spring 142 to propel the piston assembly to then propel the plunger 134, as further discussed below.

As shown, a trigger 150 overlies the latch piece 144, which seats in a cutout or recessed section of the trigger 150. The trigger 150 and the latch piece 144 may both be pivotable about the same pin 146, which can be held at ends thereof by receiving holes formed on two spaced apart side flanges (not shown). In an example, the housing 106 can be provided with two spaced apart wall structures or flanges each with an opening for receiving a respective end of the pivot pin 146. The flanges can be machined with the housing 106, or be attached to the housing, such as by welding or by fasteners. The trigger 150 lengthens the extension of the latch piece 144 to provide additional leverage when depressing the trigger to rotate the latch piece 144 to then release the drive spring. A safety mechanism, such as a movable ring or a safety pin, may be used to obstruct the trigger and wherein the safety mechanism can be moved or removed, such as slid away from the trigger, before the trigger can be activated.

In some examples, a return spring (not shown) can be provided between the trigger 150 and the housing 106, at the complementary receiving area 156. The return spring biases the contact end of the trigger 150 away from the housing 106 so that the trigger pushes the latch piece 144 downward into the side opening 148 to engage the piston head 140 to thereby hold the drive spring 142 in the compressed state. Thus, when the trigger is pressed to release the primary or drive spring 142, the return spring can push the trigger upward, or the opposite direction, to then push the latch piece 144 downwardly so that the primary spring 142 can be reset for another needleless injection, as further discussed below.

The drive spring 142 is biased between the end plug 118 and the piston head 140, as previously discussed. It has been found that the coiled spring 142 should develop approximately 25 pounds or greater force in order propel the piston system 180 (FIG. 5) to then propel the plunger 134 to generate sufficient discharge pressure at the discharge tip 154 of the ampoule 116, to penetrate a wide range of skin thickness with just fluid jet pressure without a needle. The spring pressure can vary depending on the injection site. For example, when used to apply numbing medicines for dental procedures or to apply hyaluronic acid to the facial area which has softer and/or thinner skin, or when performing an intradermal injection, the spring pressure can be less than 25 pounds to generate less delivery force at the discharge end. Preferably, the spring 142 in combination with the length of the piston system 180 (FIG. 5) and the length of the plunger 134 inside the ampoule 116 should have sufficient length to generate the driving spring force at the discharge tip 154. In other words, the drive spring 142 can be calibrated to operate between two ends of its full stroke.

A piston rod 158 passes through the passage or bore 160 of the end plug 118. The passage or bore 160 should have a sufficient inside diameter (ID) so that the shaft of the piston rod 158 can slide with adequate clearance. The piston rod 158 has a head section 162 and a rod or shaft section 163. The head section 162 has a push surface 166 (FIG. 8) that contacts the plunger 134 to move the plunger when the spring 142 is released, as further discussed below. The rod or shaft 163 has an overall length measured from the end most proximal end to where the rod connects to the head section 162. Part of the overall length of the rod 163 extends proximally of the proximal end of the housing 106, which may be referred to as a control rod section 170.

The control rod section 170 can vary in length depending on the position of the piston rod 158 relative to the piston head 140. For example, once the spring 142 is loaded or cocked by compressing the drive spring and then holding the drive spring in the compressed state by the engaging the piston head 140 with the latch piece 144, a length of the control rod section 170 extends out the end plug 118. The length of the control rod section 170 that extends proximally out of the end plug can vary as the piston rod 158 can independently move relative to the piston head 140 by adjusting the control rod section 170. In an example, the piston rod 158 is threadedly engaged to a coupling sleeve 174 (FIGS. 5 and 7) of the piston system 180 and the coupling sleeve 174 can fix to the piston head 140 such that the sleeve 174 and the piston head 140 do not move relative to one another, such as by interference fit, by using a set screw, by welding, or a combination thereof. Thus, when the control rod section 170 is gripped and rotated, its position relative to the coupling sleeve 174 and to the piston head 140 moves or shifted. For example, when the control rod section 170 is rotated in a clockwise direction, the rod or shaft 163 can advance in the distal direction to then move the head section 162 of the piston rod 158 in the distal direction relative to the piston head 140. This in turn pushes on the plunger 134 to advance the plunger further within the ampoule 116 without releasing the spring 142. In practice, by adjusting the plunger rod 158, a user can adjust the volume within the ampoule 116 or can dispense trapped air within the ampoule before using the needleless injector 100 on a patient. In an example, the proximal end, at the control rod section 170, can be enlarged to facilitate gripping. Optionally, a flared end or a knurled end or finish can be provided at the proximal end to facilitate gripping the proximal end. Still alternatively, a sleeve can be placed over the proximal end to provide a tactile grip.

In an example, the control rod section 170 can be rotated counter-clockwise relative to the coupling sleeve 174 to move the rod or shaft 163 in the proximal direction and clockwise to move the rod 163 in the distal direction relative to the coupling sleeve 174. In alternative embodiments, the rotation direction and the rod movement direction can reverse. As used herein, distal end denotes an end closer to where fluid exits the ampoule, and the proximal end is the opposite end.

In an alternative and more preferred embodiment, the piston rod 158 can be fixed to the coupling sleeve 174 such that the piston rod and the coupling sleeve do not move relative to one another. For example, the piston rod 158 and the coupling sleeve 174 can engage by interference fit, by crimping, by set screw, or equivalents, such that the two do not move relative to one another. The coupling sleeve 174 is then threadedly engaged to the threaded bore of the piston head 140 such that rotation of the control rod section 170 changes the threaded engagement between the coupling sleeve 174 and the threaded bore of the piston head 140. This is shown in FIG. 4 and further discussed below. That is, when the control rod section 170 is rotated clockwise, both the piston rod 158 and the coupling sleeve 174 advance within the threaded bore of the piston head 140 to advance the head section 162 of the piston rod in the distal direction. In still yet other examples, the piston rod 158 can threadedly engage the piston head 140 directly without utilizing the coupling sleeve 174. Again, the rotation direction and the rod movement direction can reverse such that a counter-clockwise direction advances the piston rod in the distal direction.

When mounting the discharge end 104 to the drive end 102, as shown in FIG. 1, the plunger 134 extends out the proximal end of the ampoule 116. Depending on the length of the plunger 134, how much medication is filled in the interior of the ampoule 116, or both, the proximal end-most point of the plunger 134 can either push against the piston system 180 (FIG. 5) and force some medication to discharge out the discharge tip 154, can mate up to the push surface 166 of the piston system 180, or can be spaced from the push surface 166 of the piston system 180, as shown in FIG. 2 and further discussed below.

The needleless injector 100 can be configured, such as sized and shaped, so that when the ampoule 116 is filled to a maximum filled line, the length of the plunger 134 that extends out the ampoule 116 just mate up to the push surface 166 of the piston system 180 without the piston system pushing against the plunger 134 to discharge some liquid out the discharge tip 154 of the ampoule. Nonetheless, a user may still want to adjust the piston rod 158 by rotating the control rod section 170 to move the head section 162 and the push surface 166 closer to or into contact with the end surface of the plunger 134. Further movement of the head section, by moving the piston rod relative to the piston head, can move the plunger to force out air that may be trapped in the ampoule. Optionally, the user may want to purposely dispense some medications to get down to a desired dosage before performing the needleless injection. To do so, the user can grab the control rod section 170 and rotate to advance the head section 162 of the piston rod 158 into the plunger 134 to move the plunger further into the ampoule, to dispense some medications out the distal tip 154.

In an example, when the piston rod 158 is adjusted to either dispense trapped air in the ampoule and/or to dispense medications to get down to a desired dosage inside the ampoule 116, the piston head 140 and/or the head section 162 is in contact with the plunger 134 prior to depressing the trigger 150 to release the drive spring 142. Thus, upon actuating the trigger 162 to release the spring 142, no impulse impact is made by the propelling the piston system 180 against the plunger 134, by not having a gap between the two, which can reduce sound emitted by the needleless injection process. In other examples, a gap can be provided between the piston system 180 and the plunger 134, which will successfully discharge liquid out the discharge end 154 of the ampoule 116 with sufficient force to perform a subcutaneous needleless injection, but possibly with a louder sound.

FIG. 2 shows a needleless injector 100 having a drive end 102 and a delivery or discharge end 104, similar to the device of FIG. 1. In the present embodiment, the ampoule 116 is filled with a lower or smaller volume and therefore the plunger 134 and the plunger tip 182 attached to the plunger 134 are located further distally inside the ampoule. Thus, there is a gap 184 between the proximal end-most part of the plunger 134 and the head section 162 of the plunger system 180 compared to the needleless injector 100 of FIG. 1. As previously discussed, the trigger 150 can be activated to discharge the spring 142, with the gap 184 prior to releasing the drive spring 142. However, the piston rod 158 can be adjusted to take up the gap before the trigger 150 is activated, as further discussed below.

FIG. 3 shows a needleless injector 100 having a drive end 102 and a delivery or discharge end 104, similar to the device of FIGS. 1 and 2. In the present embodiment, the ampoule 116 is filled with a lower or smaller volume compared to that of FIGS. 1 and 2, and therefore the plunger 134 and the plunger tip 182 attached to the plunger 134 are located further distally inside the ampoule. Thus, there is normally a gap between the proximal end-most part of the plunger 134 and the head section 162 of the plunger system 180. However, as shown, the piston rod 158 has been adjusted by rotating the control rod section 170 to advance the piston rod 158, and the coupling sleeve 174 that the piston rod is attached to, relative to the piston head 140 to take up the gap before the trigger 150 is activated. Consequently, the control rod section 170 of the rod or shaft 163 that extends out the end plug 118 is shorter than that of FIGS. 1 and 2.

FIG. 4 shows a needleless injector 100 having a drive end 102 and a delivery or discharge end 104 similar to FIG. 3, but shown without the drive spring 142 for clarity. As shown, the head section 162 of the piston rod 158 is advanced distally of the piston head 140, compared to that of FIGS. 1 and 2. As the piston rod 158 is secured to the coupling sleeve 174, the distal end 174a of the coupling sleeve 174 moves further distally of the piston head 140 and the proximal end 174b of the coupling sleeve 174 moves closer to the piston head 140. To prevent over rotation and possibly causing the coupling sleeve 174 to completely separate from the piston head 140, the coupling sleeve 174 and/or the piston head 140 may incorporate limiting features to stop the relative rotation between the two, such as pins, rods, flat portions without threads, projections, etc. Again, alternative embodiments of the present invention include directly threading the piston rod 158 to the piston head 140 without the coupling sleeve 174.

From the position shown in FIG. 4, a user depressing the trigger 150 will cause the latch piece 144 to rotate about the pivot pin 146 to then separate from the piston head 140. No longer held by the latch piece 144, the spring force of the drive spring 142 (FIGS. 1-3) expands to propel the piston system 180, which includes the piston rod 158, coupling sleeve 174, and piston head 140, in the distal direction. This movement causes the head section 162 to push against the end surface 188 of the plunger 134 to advance the plunger in the distal direction with sufficient force such that the plunger tip 182, which slidingly seals against the interior of the ampoule, to then force medications contained in the ampoule to expel out the discharge tip 154 to then penetrate under the skin to deposit discharged medications under the skin.

Distal travel of the head section 162 can stop when the trigger 150 is activated by sizing the head section 162 to contact or abut the collar 126 (FIG. 1) in the interior of the housing 106. Doing so can prevent the piston system 180 from driving the plunger tip 182 violently or excessively into the discharge end of the ampoule.

FIG. 5 is a schematic partial cross-sectional side view of the piston system 180 usable with the needleless injector 100 of FIGS. 1-4. The piston head 140 is shown with a threaded bore 190 for threaded engagement with the exterior threads of the coupling sleeve 174. A recessed cavity 192 is provided at the distal end of the piston head 140 for receiving the head section 162 of the piston rod 158. The recessed cavity 192 is sufficiently shallow and wide to receive the head section 162 so that the push surface 166 of the head section 162 is exposed for abutting contact with the end surface 188 of the plunger 134. In some examples, the recessed cavity 192 is eliminated and the piston head 140 comprises the threaded bore 190 only. In this alternative embodiment, the proximal side of the head section 162 can abut or contact the distal end surface of the piston head 140 when the piston system 180 is in the corresponding position as shown in FIG. 5.

In an example, the length of the coupling sleeve 174 is about two times to about five times the length of the threaded bore 190 of the piston head 140. In other examples, the length of the coupling sleeve can be greater than five times longer, such as six to eight times longer. The length of the coupling sleeve 174 relative to the length of the threaded bore 190 controls the length of adjustment that the control rod section 170 can be rotated to move distally to push the plunger in the distal direction, after the drive spring 142 is loaded or cocked. A large range of adjustment allows the plunger 134 to move within the ampoule 116 to adjust the fluid contents within the ampoule from a full ampoule to about 20% of the total volume. For example, the contents of the ampoule can be adjusted from about 0.50 mL down to about 0.10 mL. In other examples, the contents can be adjusted down to a lower volume, such as down to about 0.05 mL. The size of the ampule can be modified accordingly to accommodate dosages other than as described, which may require also adjusting the spring constant and plunger size.

FIG. 6A is a perspective side view of the piston head 140 and FIG. 6B is a cross-sectional side view thereof. In an example, a plurality of spaced apart channels 196 are formed on the exterior of the piston head. The channels 196 can each extend lengthwise, the same direction as the bore 190. The channels can provide venting to minimize possible vapor or air lock when the piston head 140 is propelled by the drive spring 142 (FIGS. 1-3). In other examples, the channels can be omitted and the outside diameter of the piston head 140 can be sized with the interior diameter of the housing 106, to allow sufficient clearance therebetween, to permit venting without the channels. In still other examples, the interior of the housing can be provided with vent channels. The piston head 140 can be machined from a metal material, such as stainless steel.

FIG. 7 is a schematic cross-sectional side view of the coupling sleeve 174. As shown, the coupling sleeve 174 has exterior threads 198 (shown schematically) for engaging the threaded bore 190 of the piston head 140. The threads in the bore 190 of the piston head 140 and on the exterior of the sleeve 174 are complementary and can range from course threads to fine threads to enable either coarse adjustments or fine adjustments. The coupling sleeve 174 has a bore 175 for receiving the rod or shaft 163 of the piston rod 158, in an interference or in a fixed arrangement, such as with a set screw, adhesive, tongue and groove, and equivalents thereof.

FIG. 8 is a side view of the piston rod 158 of FIGS. 1-5. As shown, the piston rod 158 has an elongated rod or shaft 163, a head section 162 at a distal end of the shaft, which is generally disc-shape with a push surface 166 at a distal end thereof. The head section 162 has a diameter that is about 1.5 to 4 times the diameter of the shaft 163. The piston rod 158 can be made from a composite or a thermoplastic material. Where the piston rod 158 threads directly to the threaded bore of the piston head 140 without the coupling sleeve 174, the piston rod 158 can be made from a composite, a thermoplastic material, or a metal material.

FIG. 9 is a schematic side view of a discharge end 104 of the needleless injector of FIGS. 1-4. The discharge end 104 comprises an ampoule 116 and a plunger 134 slidably disposed within the interior 202 of the ampoule. The ampoule 116 comprises a barrel 204 having an enclosed distal end 206 with a discharge tip 154 having a passage or orifice 208 extending therethrough defining a nozzle. The passage or orifice 208 is in fluid communication with the interior 202 and liquid in the interior, such as medications, can dispense out through the nozzle when pressurized by the propelling plunger 134. The nozzle opening or size can be between about two thousandths to about six thousandths of an inch but can vary depending on the generated velocity and pressure for performing a needleless injection. In an example, the inside diameter of the barrel is about 0.18-inches and the length from the flange 212 to the enclosed distal end is about 1.4-inches. The ampoule can accommodate or hold up to about 0.50 mL. However, these values are exemplary only as the size of the ampoule can vary, such as holding up to about 0.30 mL only or greater than 0.50 mL.

The threaded end 122 at the proximal end of the barrel 204 comprises male threads for engaging corresponding female threads of the threaded receiving socket 120 of the drive end 102. The flange 212 can serve as a physical stop for the engagement but the threaded end 122 can instead bottom out in the receiving socket 120 before the flange 212 is contacted by the rim of the first open end 112.

The ampoule 116 may be made from a hard but brittle-resistant thermoplastic material. The ampoule may be made from plastic injection molding, such as with polycarbonate (PC), ABS, LEXAN, or Acrylic, as non-limiting examples. The exterior of the barrel 204 can be provided with markers or scales 214, such as 0.10 mL, 0.20 mL, etc., to aid in measuring the volume of medications added to the interior 202 of the barrel.

The plunger 134 is shown partially located inside the interior 202 and partially extending out the proximal opening 216 of the barrel 204. The plunger 134 has a shaft 220 with a distal end having a mounting tip that projects into a sleeve like interior of the plunger tip 182 to retain the plunger tip at the distal end of the plunger. The plunger tip 182 slidingly seals against the interior wall surface of the barrel and compresses the liquid as it advances in the distal direction to build pressure to then eject out of the nozzle 208 with sufficient velocity that it can be hypodermically injected at an injection site without a needle. The plunger tip 182 can be made from an elastomeric material, such as polytetrafluoroethylene (TPFE) or a rubber material, or a thermoplastic-elastomer (TPE) material. The plunger tip 182 can have a generally round outer cylindrical shape with a length and wherein the exterior of the plunger tip can have one or more undulating or grooved surfaces to form a discontinuous contact with the interior surface of the barrel.

The plunger 134 can be about 2.1-inches to about 2.3-inches in overall length and about 0.175-inches in diameter. In other examples, the plunger can have a different length and diameter without deviating from the scope of the invention. The plunger can be made from the same or similar material as the material of the ampoule or can be made form a different material. As shown, the plunger has an end section 188 with a plurality of spaced apart grooves 218. The grooves can be provided for aesthetic reasons but can optionally be omitted.

FIG. 10A is a schematic cross-sectional side view of a resetter 222 for resetting the primary or drive spring 142 (FIGS. 1-3) of the drive end 102 and FIG. 10B is a top view of the resetter 222. The resetter 222 comprises a base housing 224 and a cover handle 226 connected to the base housing 224 by a pin 228, which is located near the far housing end 229. The cover handle 226 has a wall surface that covers the upper opening of the base housing 224 and is shown in FIG. 10A in the raised or opened position. When rotated to close over the upper opening of the base housing 224, the cover handle 226 has approximately the same length as the base housing.

A saddle 230 is slidably mounted to the base housing 224 of the resetter 222. The saddle 230 has a push head 232 having a length and a width and the push head 232 is connected to a first pair of linkage arms 234 (only one shown). Each linkage arm 234 is shaped similar to a spatula or elongated flat stick. Each of the first pair of linkage arms 234 is in turn connected to a respective pair of second linkage arms 236 (only one shown) by a set of pins 238. Each of the second pair of linkage arms 236 is in turn connected to the cover handle 226, via two separate pins 242 or a single pin 242 that connects to both linkage arms 236 of the second pair. The upper pin 242 can snap into a pin receptacle secured to or unitarily formed with the cover handle 226. Thus, when the cover handle 226 moves to the raised position shown in FIG. 10A, the first and second pair of linkage arms are moved by the cover handle and therefore move the push head 232 to the first or retraced position shown. When the cover handle 226 is lowered to a closed position, the linkage arms 234, 236 move the push head 232 to the second or load position, which moves to the left of the far housing end 229 from the current position shown in FIGS. 10A and 10B.

A press rod or shaft 246 is mounted to the push head 232. Thus, when the push head 232 moves between the first position or the retracted position (FIG. 10A) and the second position or the load position further left of the far housing end 229, due to movement of the cover handle 226 and the linkage arms 234, 236, the movement moves the press rod 246 left of its current position shown in FIGS. 10A and 10B. This movement of the press rod 246 can be used to reset the drive spring, as further discussed below.

With reference again to FIGS. 10A and 10B and to the needleless injector of FIGS. 1-3, the drive end 102 can be reset using the resetter 222 for re-use after the drive spring 142 is released by the trigger 150. As shown, the housing 106 of the drive end 102 is positioned in the loading space 250 of the base housing 224 with the open end 130 of the housing 106 oriented towards the push head 232 and the press rod 246 projecting through the open end 130 and into the housing of the drive end. The free end of the press rod 246, the end opposite the end that attaches to the push head 232, is placed in contact with or in close proximity to the piston system 180, and more particularly to the push surface 166 of the piston rod 158.

From the position of FIGS. 10A and 10B, the cover handle 226 can be rotated counter-clockwise about the pin 228 from the orientation shown to close the cover handle 226 over the base housing 224. This motion moves the two pairs of linkage arms 234, 236 and the linkage arms move the push head 232 from the retracted position to the load position, which moves the press rod 246 to push the head section 162 of the piston rod 158 and the piston head 140 towards the end plug 118 of the drive end to compress the drive spring 142. As the piston head 140 moves proximal of the latch piece 144 by the press rod 246 of the resetter 222, the tip of the latch piece 144, acted on by the return spring, moves in front of the piston head 140 to hold the drive spring 142 in the compressed position. This action causes the drive spring 142 to be reset or cocked so that the drive end 102 can be used for another subcutaneous injection.

After the drive spring is reset, the cover handle 226 can be lifted, raised, or rotated in the clockwise direction to open the resetter 222 to thereby allow the drive end 102 to be removed from the loading space 250 of the base housing 224. To use the drive end 102 that has now been reset using the resetter 222, an ampoule 116 filled with medications can be threaded into the open threaded receiving socket 120 of the housing 106 of the drive end 102, as previously discussed.

FIG. 11A is a perspective view of a vial adaptor 260 and FIG. 11B is a cross-sectional side view of the vial adaptor 260. The vial adaptor 260 is sized and shaped to couple an ampoule 116, such as the ampoule of FIGS. 1-4 and 9, to enable filling the interior 202 of the ampoule with a medicament or medication from a vial 300 (FIG. 13). As shown, the vial adaptor 260 comprises a plurality of prongs 264. In an example, the prongs 264 are spaced apart and together define a holding space or receiving space 266 for receiving the distal end 206 of the ampoule 116. In an example, each prong 264 is generally rectangular and arcuate or arc shape. The plurality of prongs 264 together defining a generally round collar having gaps 268 between adjacent prongs 264.

In an example, four prongs 264 are provided extending above a flange 270. In an example, the four prongs 264 have two sets of two prongs that are the same. For example, two opposing taller prongs 264a extend higher above the flange than two opposing shorter prongs 264b. Each of the two sets of prongs 264a, 264b has a detent or radial lip 272. Thus, the two taller prongs 264a have radial lips 272 that are elevated higher than the radial lips 272 of the shorter prongs 264b. The different heights are incorporated for the two different radial lips 272 to engage different thread sections 276, 278 located at the distal end of the ampoule 116. Thus, when the distal end of the ampoule 116 is placed into the receiving space 266 of the vial adaptor 260, the different radial lips can grip the differently arranged thread sections 276, 278 located on the ampoule. If the ampoule has different threads or flange sections at the distal end, the prongs and the radial lips can be adjusted accordingly to mate between the two.

The flange 270 on the vial adaptor 260 has a raised central rim 276 and a central bore 280. The raised central rim 276 is sized and shaped to surround and abut the raised distal tip 154 (FIG. 9) of the ampoule to form a tight connection with the ampoule. A cannula 282 having a sharp tip 284 and an opening 286 is provided at an end of the cannula 282. The opening 286 at the tip is in fluid communication with the lumen 288 passing through the cannula 282. The cannula 282 has a length measured from its base 290 to the sharp tip 284. The length of the cannula 282 can be selected to fit a range of vial sizes.

FIG. 12 shows an ampoule 116 engaged to a vial adaptor 260, with the cannula 282 and the ampoule only partially shown. The ampoule 116 can be similar to the ampoule of FIG. 9 and the vial adaptor can be similar to the vial adaptor of FIGS. 11A and 11B. In an example, the ampoule 116 can comprise a flange 294 and a continuous or spaced apart mounting flange sections 296 located distally of the flange 294 and having a gap 298 therebetween. The mounting flange sections 296 is configured to be gripped by the prongs 264 on the vial adaptor 260 and the radial lips or detents 272 can project into the gap 298 to grip the ampoule. The ampoule can engage the vial adaptor using the quick snap connection of the prongs. In other examples, the vial adaptor can incorporate a threaded receptacle to threadedly engage the ampoule.

FIG. 13 shows the combination ampoule 116 and vial adaptor 260 having the cannula 282 projected through the resealable septum 302 of the vial 300 and in fluid communication with medicament or medications 304 located in the interior of the vessel or housing 306. Once in the position shown, the plunger and plunger tip (not shown) located inside the ampoule can be retracted to create a vacuum to fill the interior 202 of the ampoule with medications to be used for a subcutaneous injection without a needle.

Methods of making and of using needleless injectors, vial adaptors, and resetters and components thereof discussed herein are within the scope of the present invention.

Although limited embodiments of the needleless injectors, adaptors, and resetters and their components have been specifically described and illustrated herein, many modifications and variations will be apparent to those skilled in the art. Accordingly, it is to be understood that the needleless injectors, adaptors, and resetters and their components constructed according to principles of the disclosed device, system, and method may be embodied other than as specifically described herein. The disclosure is also defined in the following claims.

What is claimed is:

1. A needleless injector comprising:
   a force generator comprising a housing with a body having a distal end with an opening, a proximal end enclosed by an end wall having a passage, a side opening, and an interior;
   a drive spring compressed between the end wall and a piston head having a bore, said piston head being held by a latch piece having a length and a width and pivotably mounted to the housing and holding the piston head against a bias of the drive spring in a ready to use position;
   a piston rod located in the bore of the piston head, said piston rod having a shaft and a head section, wherein the shaft extends out the passage of the end wall and the head section having a push surface;
   a coupling sleeve having a bore and having the shaft of the piston rod located in the bore;
   wherein the shaft that extends out the passage is rotatable to move the piston rod relative to the piston head and move the push surface away from the piston head in the ready to use position; and
   wherein the coupling sleeve has exterior threads threadedly engaged with threads in the bore of the piston head.

2. The needleless injector of claim 1, wherein the latch piece projects through the side opening to hold the piston head in the ready to use position.

3. The needleless injector of claim 2, further comprising a trigger pivotably mounted to the housing and in contact with the latch piece for rotating the latch piece.

4. The needleless injector of claim 1, wherein the end wall is on an end plug and the end plug is threadedly engaged to the housing.

5. The needleless injector of claim 1, further comprising a collar having a passage, the collar being located in the interior of the housing for stopping distal advancement of the piston head.

6. The needleless injector of claim 1, wherein the piston head has an exterior and a recessed cavity and wherein the head section of the piston rod is located in the recessed cavity in the ready to use position.

7. The needleless injector of claim 6, wherein the recessed cavity has a diameter and a depth and wherein the depth is greater than a thickness of the head section.

8. The needleless injector of claim 6, further comprising a plurality of spaced apart channels located on the exterior of the piston head.

9. The needleless injector of claim 6, wherein the piston rod is made from a thermoplastic or a composite material and the piston head is made from a metal material.

10. The needleless injector of claim 1, wherein the shaft of the piston rod and the coupling sleeve are fixed from relative movement of one another.

11. The needleless injector of claim 1, wherein the piston head has a length and wherein the coupling sleeve has a length that is longer than the length of the piston head.

12. The needleless injector of claim 1, wherein the coupling sleeve is made from a metal material and the piston head is made from a metal material.

13. The needleless injector of claim 1, further comprising a discharge end comprising an ampoule having a barrel with a discharge tip having an orifice and a plunger slidably disposed within the barrel, said barrel being coupling to the housing.

14. The needleless injector of claim 13, wherein the barrel is threadedly engaged to the housing.

15. The needleless injector of claim 13, wherein the discharge tip is tapered.

16. The needleless injector of claim 13, further comprising a plunger tip attached to a distal end of the plunger.

17. The needleless injector of claim 13, wherein the plunger has an end section with an end surface and wherein the end surface of the plunger is spaced from the push surface in the ready to use position.

18. The needleless injector of claim 13, wherein the plunger has an end section with an end surface and wherein the end surface of the plunger is in contact with the push surface in the ready to use position.

19. A method for manufacturing a needleless injector comprising:
   forming a force generator comprising a housing with a body having a distal end with an opening, a proximal end enclosed by an end wall having a passage, a side opening, and an interior;
   placing a drive spring in the interior of the body between the end wall and a piston head having a bore;
   holding the drive spring in a compressed state in a ready to use position by holding the piston head with a latch piece having a length and a width and pivotably mounted to the housing to hold the piston head against a bias of the drive spring;

placing a piston rod having a shaft and a head section in the bore of the piston head so that the shaft extends out the passage of the end wall; and wherein the shaft that extends out the passage is rotatable to move the piston rod relative to the piston head and move the push surface away from the piston head in the ready to use position;

wherein a coupling sleeve having a bore and having the shaft of the piston rod located in the bore; and wherein the coupling sleeve has exterior threads threadedly engaged with threads in the bore of the piston head.

* * * * *